United States Patent
Singh

(10) Patent No.: US 11,681,789 B2
(45) Date of Patent: Jun. 20, 2023

(54) ELECTROENCEPHALOGRAM HASHING DEVICE FOR AUTHENTICATION AND ROUTING

(71) Applicant: Bank of America Corporation, Charlotte, NC (US)

(72) Inventor: Shailendra Singh, Maharashtra (IN)

(73) Assignee: Bank of America Corporation, Charlotte, NC (US)

( * ) Notice: Subject to any disclaimer, the term of this patent is extended or adjusted under 35 U.S.C. 154(b) by 376 days.

(21) Appl. No.: 16/930,599

(22) Filed: Jul. 16, 2020

(65) Prior Publication Data

US 2022/0019647 A1 Jan. 20, 2022

(51) Int. Cl.
| | |
|---|---|
| *G06F 21/32* | (2013.01) |
| *A61B 5/117* | (2016.01) |
| *H04L 9/06* | (2006.01) |
| *H04L 9/40* | (2022.01) |
| *G16H 10/60* | (2018.01) |
| *G16H 40/67* | (2018.01) |
| *G16H 50/70* | (2018.01) |
| *G06Q 20/38* | (2012.01) |
| *G06Q 20/40* | (2012.01) |
| *G06Q 20/10* | (2012.01) |

(Continued)

(52) U.S. Cl.
CPC ............. *G06F 21/32* (2013.01); *A61B 5/117* (2013.01); *A61B 5/378* (2021.01); *A61B 5/38* (2021.01); *A61B 5/381* (2021.01); *G06F 21/35* (2013.01); *G06Q 20/1085* (2013.01); *G06Q 20/3223* (2013.01); *G06Q 20/3825* (2013.01); *G06Q 20/3827* (2013.01); *G06Q 20/40145* (2013.01); *G16H 10/60* (2018.01); *G16H 40/67* (2018.01); *G16H 50/70* (2018.01); *H04L 9/0643* (2013.01); *H04L 63/0428* (2013.01); *H04W 12/033* (2021.01)

(58) Field of Classification Search
CPC ......... G06F 21/32; G06F 21/35; G16H 40/67; G16H 10/60; G16H 50/70; A61B 5/38; A61B 5/381; A61B 5/378; A61B 5/117; H04W 12/033; G06Q 20/1085; G06Q 20/3223; G06Q 20/3825; G06Q 20/3827; G06Q 20/40145; H04L 63/0428; H04L 9/0643
See application file for complete search history.

(56) References Cited

U.S. PATENT DOCUMENTS

| | | | |
|---|---|---|---|
| 10,169,560 B2 * | 1/2019 | Cudak | G06F 21/32 |
| 10,437,332 B1 * | 10/2019 | Paterson | G06F 40/166 |

(Continued)

*Primary Examiner* — Richard A McCoy
(74) *Attorney, Agent, or Firm* — Weiss & Arons LLP; Michael A. Springs, Esq.

(57) ABSTRACT

Systems and methods for authenticating and/or routing a digital signal are provided. A system may include a central database configured to store a set of signature brain wave responses as part of a profile of a user. The system may include a transaction device, a sensory device, and an EEG device. When a transaction request is received from the user, the system may be configured to present the user with a sensory prompt, detect a response of the user to the first sensory prompt, compare the response to the signature response in the profile associated with the sensory prompt, and, when the response matches the signature response within a predetermined delta, authenticate and/or route the transaction request.

13 Claims, 7 Drawing Sheets

(51) Int. Cl.
*G06Q 20/32* (2012.01)
*G06F 21/35* (2013.01)
*A61B 5/38* (2021.01)
*A61B 5/378* (2021.01)
*A61B 5/381* (2021.01)
*H04W 12/033* (2021.01)

(56) References Cited

U.S. PATENT DOCUMENTS

| | | | |
|---|---|---|---|
| 2006/0024335 A1* | 2/2006 | Roger | A61K 9/0056 424/400 |
| 2015/0137988 A1* | 5/2015 | Gravenstein | A61B 5/14551 702/19 |
| 2015/0199010 A1* | 7/2015 | Coleman | A61B 5/165 345/156 |
| 2015/0366518 A1* | 12/2015 | Sampson | A61B 5/7275 600/509 |
| 2019/0132733 A1* | 5/2019 | Castinado | G16H 30/40 |
| 2019/0192083 A1* | 6/2019 | Laszlo | G06N 20/00 |
| 2020/0205712 A1* | 7/2020 | Laszlo | A61B 5/377 |

* cited by examiner

ELECTROENCEPHALOGRAM HASHING DEVICE FOR AUTHENTICATION AND ROUTING

FIELD OF TECHNOLOGY

Aspects of the disclosure relate to computer systems. Specifically, aspects of the disclosure relate to systems and methods for authenticating and routing digital signals.

BACKGROUND OF THE DISCLOSURE

Digital signals are commonly used to transmit sensitive information. For example, digital signals are often used to transmit requests that may relate to the health and/or finances of the signal initiator. Digital signals that are hacked, co-opted, misrouted, or in other ways defective may jeopardize the health and/or finances of the purported signal initiator.

For example, a digital signal may be received by a financial institution. The digital signal may indicate that an account user is requesting a certain transaction, e.g., a withdrawal at an automated teller machine (ATM). Conventional systems for authenticating the signal may include reading a card and/or entering personal identification number (PIN). Conventional systems for routing the signal may include pressing a button on a keypad or touchscreen.

However, cards are vulnerable to theft or duplication without authorization. PIN numbers are sometimes obtained without permission. Touchscreens and keypads may freeze, stick, or otherwise break. Users, especially the elderly and those with physical or mental difficulties, may enter routing, or other, instructions they do not really intend. Such signals, if mistaken and/or not properly authenticated or routed, may result in funds being withdrawn or otherwise misdirected without permission or intention of the account user.

It would be desirable therefore, to provide systems and methods capable of providing secure authentication of sensitive digital signals.

It would be further desirable for the systems and methods to be capable of accurate routing of sensitive digital signals.

SUMMARY OF THE DISCLOSURE

Aspects of the disclosure relate to secure methods for authenticating and/or routing a digital signal. A method may include recording a set of signature responses of a user. Each signature response from the set of signature responses may include a pattern of brain activity detected by an electroencephalogram (EEG) when the user is presented with a sensory prompt from a set of sensory prompts. The method may include storing the set of signature responses in a central database as part of a profile of the user.

The method may include receiving a request from the user to initiate a transaction, presenting to the user a first sensory prompt from the set of sensory prompts, and detecting, via an EEG, a response of the user to the first sensory prompt, the response including a pattern of brain activity.

The method may also include comparing the response to the signature response in the profile associated with the first sensory prompt. When the response matches the signature response within a predetermined delta, the method may include authenticating and/or routing the transaction.

BRIEF DESCRIPTION OF THE DRAWINGS

The objects and advantages of the disclosure will be apparent upon consideration of the following detailed description, taken in conjunction with the accompanying drawings, in which like reference characters refer to like parts throughout, and in which.

DETAILED DESCRIPTION OF THE DISCLOSURE

Figure 1:
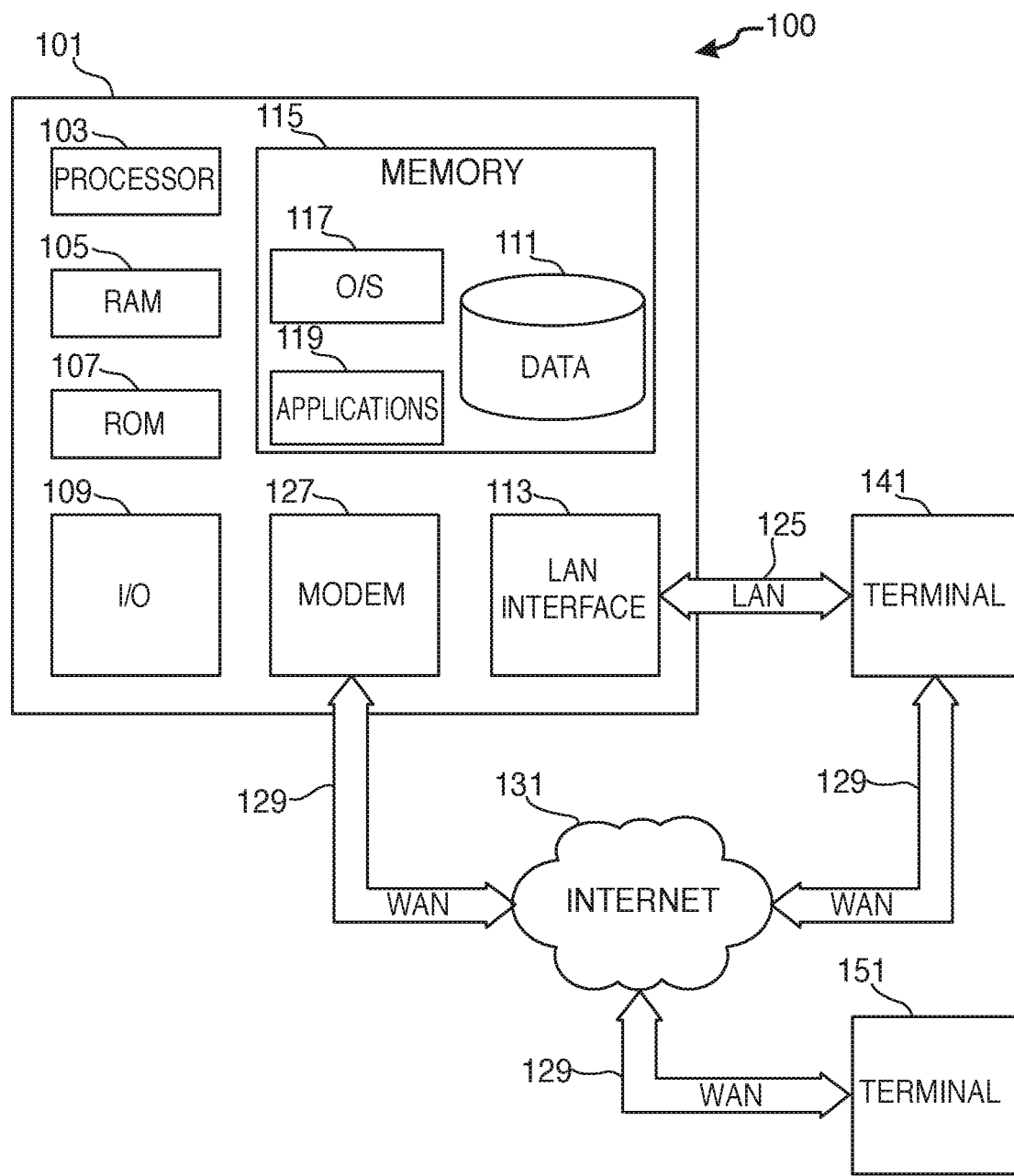
FIG. 1 shows an illustrative system in accordance with principles of the disclosure.

Systems and methods for secure authentication and/or accurate routing of digital signals are provided. The digital signal may, for example, be a sensitive request signal. A sensitive request signal may, for example, be a signal requesting a financial transaction. Other exemplary signals may include other suitable messages or requests, especially ones that, if misdirected or fraudulent in nature, may incur damage and/or loss.

The systems and methods may include a platform. The platform may include and/or be connected to a central database. The central database may be configured to store a set of signature responses as part of a profile of a user.

The set of signature responses may, in some embodiments, be recorded after the user opts-in to use the platform. For example, the user may be provided an option to opt-in via a website or mobile application ("app") accessible on a mobile device. The website or app may be associated with an entity, such as a financial institution, that is associated with the central database. The user may also, in certain embodiments, opt-in at a physical location of the entity.

Each signature response from the set of signature responses may include a pattern of brain activity detected by an electroencephalogram (EEG). The EEG may, in certain embodiments, be a part of (or otherwise connected to) a user device, such as a computer or mobile device. The EEG may be located at a location of the entity (for example, at a bank location). In some embodiments, the entity may have an agreement with a medical facility to utilize EEGs of the facility to detect the signature responses.

The pattern of brain activity of the signature responses may be detected by the EEG when the user is presented with a sensory prompt from a set of sensory prompts. The sensory prompt may, in certain embodiments, include an image prompt, a text prompt, an audio prompt, a video prompt, a scent prompt, a touch prompt, and/or a taste prompt. The sensory prompt may include an actual physical object. The object may be in the presence of the user, or, in some embodiments, not in the presence of the user. The sensory prompt may be a prompt to think about an object or a concept.

The sensory prompts may be presented by the entity. The sensory prompts may be presented at a physical location of the entity. The sensory prompts may be presented via a mobile device, e.g., via an app provided by the entity.

Detecting, recording, and/or storing the signature responses may be part of a training, or tuning, of the platform. Tuning the platform may train the platform with the brain wave patterns this particular user typically emits when presented the sensory prompts. The brain wave patterns may represent a physiological manifestation of an emotional response of the user to the prompts. Each user may have a unique signature response to the prompts. In other embodiments, any other suitable detectable, unique, bio-signals may be utilized by the platform.

The platform may include a transaction device. The transaction device may be configured to receive a transaction request. The platform may include a sensory device. The sensory device may be configured to present to the user a sensory prompt. The platform may also include an EEG device. The EEG device may be configured to detect brain activity of the user.

In one illustrative embodiment of the platform, the transaction device may be an automated teller machine (ATM). The sensory device may be an app running on a computing device such as a mobile phone. The sensory device may be coupled to the ATM or the central server, e.g., via a cable, Bluetooth, WiFi, or other suitable form of connectivity. In some embodiments, the transaction device and the sensory device may be the ATM. In some embodiments, the transaction device and the sensory device may be the computing device.

The EEG may be any suitable device for detecting brain wave activity. The EEG may include a headpiece. The headpiece may include a plurality of electrical leads. The headpiece may resemble a hood, helmet, headphones, or any other suitable EEG headpiece. The EEG may be connected, with wires or wirelessly, to the transaction device and/or the sensory device. It is contemplated that an EEG capable of detecting brain wave activity from a distance may be provided as a built-in component of the transaction device and/or the sensory device. The built-in EEG may be able to detect the brain activity of the user without contacting the.

When a transaction request is received from the user via the transaction device, the platform may be configured to present the user, via the sensory device, with a first sensory prompt from the set of sensory prompts. For example, the platform may display a picture of a flower. The platform may play a clip of a song. The platform may show a video clip. The platform may, in certain embodiments, direct the user to focus on a physical object apart from the sensory device. For example, the platform may direct the user to focus on his or her hand, or a nearby object such as an apple.

The platform may be configured to detect, via the EEG, a response of the user to the first sensory prompt. A response may include a pattern of brain activity. The platform may be configured to compare the response to the signature response in the profile associated with the first sensory prompt. When the response matches the signature response within a predetermined delta, the platform may be configured to authenticate and/or route the transaction request.

The delta may be a percentage. For example, the predetermined delta may be that at least 95%, or any other suitable percentage, of the pattern of the response is the same as the pattern of the signature response. In some embodiments, the delta may be a confidence score. The confidence score may be the output of an artificial intelligence (AI) engine trained to compare two brain wave patterns and calculate a confidence score of the two being emitted from the same brain.

In certain embodiments of the platform, authenticating the transaction request may include matching the response to the signature response to confirm that the transaction request was transmitted by the user. Once authenticated, the transaction may be executed by the transaction device. In some embodiments, the transaction request may be a request of the user to log-in to a system through which a transaction may be requested. The authentication may validate the log-in, and the user may subsequently be enabled to request a transaction.

In some embodiments, the platform may be configured to route a transaction request. The first sensory prompt may be part of a plurality of sensory prompts presented to the user. Each of the plurality of sensory prompts may be from the set of sensory prompts used to generate the set of signature responses. To accomplish the routing, the platform may be configured to present each of the plurality of sensory prompts in conjunction with a different transaction option from a plurality of transaction options.

The user may generate the response by focusing on one of the sensory prompts that is presented in conjunction with the desired transaction option. The platform may be configured to determine which signature response is a closest match to the response. The platform may be configured to determine which sensory prompt is mapped to the signature response that is the closest match. The platform may be configured to determine which transaction option was presented in conjunction with the sensory prompt. The platform may be also configured to route the request to a central server to execute the transaction option.

As an illustrative example, the list of transaction options may include 1) Make a Deposit, 2) Make a Withdrawal, and 3) Make a Transfer. The transaction options may be shown on a display of a mobile phone or an ATM. Adjacent to each option, the platform may display a different sensory prompt—for example, a picture of a flower next to option 1), a picture of a house next to option 2), and a picture of a baby next to option 3). The user may wish to select option 3), so he or she may focus on the picture of the baby. The EEG may detect brain activity while the user focuses on the baby, and compare the pattern of the activity to the signature responses in the database. The signature responses may also include patterns detected while the user was presented with pictures of a flower, a house, and a baby. The platform may determine that the detected response most closely matches the signature response that was recorded for the picture of a baby. The platform may thus determine that the user was selecting option 3), and the platform may route a request for a Transfer.

In some embodiments, the text of each transaction option (or, in certain embodiments, the mere concept of the option itself) may also be the sensory prompt. For example, the phrases "Make a Deposit," "Make a Withdrawal," and "Make a Transfer" may each be part of the sensory prompts that were used to generate signature responses. The user may focus on one of the options, and the detected brain wave response may be matched to the signature responses to determine which option the user is focusing on, and thereby selecting.

In certain embodiments, the predetermined delta may be a first predetermined delta when authenticating the transaction, and a second predetermined delta when routing the transaction. The first predetermined delta may, in certain embodiments, be smaller than the second predetermined delta. The platform may be configured in such a manner because authentication includes comparing the current response of the supposed user to the signature response of the user, both in response to the same sensory prompt. The authentication may be more accurate when restricted to a small delta. In contrast, routing may compare a response to an as yet unknown prompt, to a set of responses of the same user to various prompts. It may be sufficient to determine the identity of the unknown prompt by allowing a larger delta, and determining the unknown prompt based on which signature prompt is closest to the current response.

The transaction device may, in certain embodiments, be an automated teller machine (ATM). The sensory device may, in some embodiments, be a part of the ATM. In other embodiments, the transaction device and/or the sensory device may be a mobile phone running an application.

In some embodiments, the platform may be further configured to hash the response with the sensory prompt to create a hashed signal. Hashing the response with the prompt may include linking the response and the prompt. The platform may be configured to transmit the hashed signal to a central server for processing. In some embodiments, the signal may be processed in the EEG device, the transaction device, and/or the transaction device.

In an exemplary embodiment, the EEG may be configured to transmit the response to the sensory device, and the sensory device may be configured to perform the hashing. The sensory device may also be configured to transmit the hashed signal to the transaction device and/or to the central server (or, in some embodiments, to the central server via the transaction device).

Methods for secure authentication and/or accurate routing of digital signals are provided. A method may include recording a set of signature responses of a user. Each signature response from the set of signature responses may include a pattern of brain activity detected by an electroencephalogram (EEG) when the user is presented with a sensory prompt from a set of sensory prompts. The sensory prompt may, for example, include an image prompt, a text prompt, an audio prompt, a video prompt, a scent prompt, a touch prompt, and/or a taste prompt. The method may include storing the set of signature responses in a central database as part of a profile of the user.

The method may include receiving a request from the user to initiate a transaction, presenting to the user a first sensory prompt from the set of sensory prompts, and detecting, via an EEG, a response of the user to the first sensory prompt, the response including a pattern of brain activity.

The method may also include comparing the response to the signature response in the profile associated with the first sensory prompt. When the response matches the signature response within a predetermined delta, the method may include authenticating and/or routing the transaction.

In some embodiments of the method, the authenticating may include matching the response to the signature response to confirm that the request was transmitted by the user.

In certain embodiments, the first sensory prompt may be part of a plurality of sensory prompts presented to the user. Each of the plurality of sensory prompts may be from the set of sensory prompts. To accomplish the routing, the method may further include presenting each of the plurality of sensory prompts in conjunction with a different transaction option from a plurality of transaction options, determining which signature response is a closest match to the response, determining which sensory prompt is mapped to the signature response that is the closest match, determining which transaction option was presented in conjunction with said sensory prompt, and/or routing the request to a central server to execute said transaction option.

In some embodiments, the predetermined delta may be a first predetermined delta when authenticating the transaction, and a second predetermined delta when routing the transaction. The first predetermined delta may, in certain embodiments, be smaller than the second predetermined delta.

In certain embodiments, the request may be transmitted by the user via an automated teller machine (ATM).

In some embodiments, the sensory prompt may be presented to the user via a mobile device.

The method may, in some embodiments, include hashing the response with the sensory prompt to create a hashed signal. The method may also include transmitting the hashed signal to a central server for processing.

In certain embodiments, the EEG may transmit the response to the device which presented the sensory prompt to the user, and the mobile device performs the hashing and transmits the hashed signal to an automated teller machine (ATM) and/or to the central server.

Apparatus and methods described herein are illustrative. Apparatus and methods in accordance with this disclosure will now be described in connection with the figures, which form a part hereof. The figures show illustrative features of apparatus and method steps in accordance with the principles of this disclosure. It is understood that other embodiments may be utilized, and that structural, functional, and procedural modifications may be made without departing from the scope and spirit of the present disclosure.

FIG. 1 shows an illustrative block diagram of system 100 that includes computer 101. Computer 101 may alternatively be referred to herein as a "server" or a "computing device." Computer 101 may be a workstation, desktop, laptop, tablet, smart phone, or any other suitable computing device. Elements of system 100, including computer 101, may be used to implement various aspects of the systems and methods disclosed herein.

Computer 101 may have a processor 103 for controlling the operation of the device and its associated components, and may include RAM 105, ROM 107, input/output module 109, and a memory 115. The processor 103 may also execute all software running on the computer—e.g., the operating system and/or voice recognition software. Other components commonly used for computers, such as EEPROM or Flash memory or any other suitable components, may also be part of the computer 101.

The memory 115 may be comprised of any suitable permanent storage technology—e.g., a hard drive. The memory 115 may store software including the operating system 117 and application(s) 119 along with any data 111 needed for the operation of the system 100. Memory 115 may also store videos, text, and/or audio assistance files. The videos, text, and/or audio assistance files may also be stored in cache memory, or any other suitable memory. Alternatively, some or all of computer executable instructions (alternatively referred to as "code") may be embodied in hardware or firmware (not shown). The computer 101 may execute the instructions embodied by the software to perform various functions.

Input/output ("I/O") module may include connectivity to a microphone, keyboard, touch screen, mouse, and/or stylus through which a user of computer 101 may provide input. The input may include input relating to cursor movement. The input/output module may also include one or more speakers for providing audio output and a video display device for providing textual, audio, audiovisual, and/or graphical output. The input and output may be related to sensitive digital signals.

System 100 may be connected to other systems via a local area network (LAN) interface 113.

System 100 may operate in a networked environment supporting connections to one or more remote computers, such as terminals 141 and 151. Terminals 141 and 151 may be personal computers or servers that include many or all of the elements described above relative to system 100. The network connections depicted in FIG. 1 include a local area network (LAN) 125 and a wide area network (WAN) 129, but may also include other networks. When used in a LAN networking environment, computer 101 is connected to LAN 125 through a LAN interface or adapter 113. When used in a WAN networking environment, computer 101 may include a modem 127 or other means for establishing communications over WAN 129, such as Internet 131.

It will be appreciated that the network connections shown are illustrative and other means of establishing a communications link between computers may be used. The existence of various well-known protocols such as TCP/IP, Ethernet, FTP, HTTP and the like is presumed, and the system can be operated in a client-server configuration to permit a user to retrieve web pages from a web-based server. The web-based server may transmit data to any other suitable computer system. The web-based server may also send computer-readable instructions, together with the data, to any suitable computer system. The computer-readable instructions may be to store the data in cache memory, the hard drive, secondary memory, or any other suitable memory.

Additionally, application program(s) 119, which may be used by computer 101, may include computer executable instructions for invoking user functionality related to communication, such as e-mail, Short Message Service (SMS), and voice input and speech recognition applications. Application program(s) 119 (which may be alternatively referred to herein as "plugins," "applications," or "apps") may include computer executable instructions for invoking user functionality related performing various tasks. The various tasks may be related to sensitive digital signals.

Computer 101 and/or terminals 141 and 151 may also be devices including various other components, such as a battery, speaker, and/or antennas (not shown).

Terminal 151 and/or terminal 141 may be portable devices such as a laptop, cell phone, Blackberry TM, tablet, smartphone, or any other suitable device for receiving, storing, transmitting and/or displaying relevant information. Terminals 151 and/or terminal 141 may be other devices. These devices may be identical to system 100 or different. The differences may be related to hardware components and/or software components.

Any information described above in connection with database 111, and any other suitable information, may be stored in memory 115. One or more of applications 119 may include one or more algorithms that may be used to implement features of the disclosure, and/or any other suitable tasks.

The invention may be operational with numerous other general purpose or special purpose computing system environments or configurations. Examples of well-known computing systems, environments, and/or configurations that may be suitable for use with the invention include, but are not limited to, personal computers, server computers, hand-held or laptop devices, tablets, mobile phones, smart phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc., that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Figure 2:
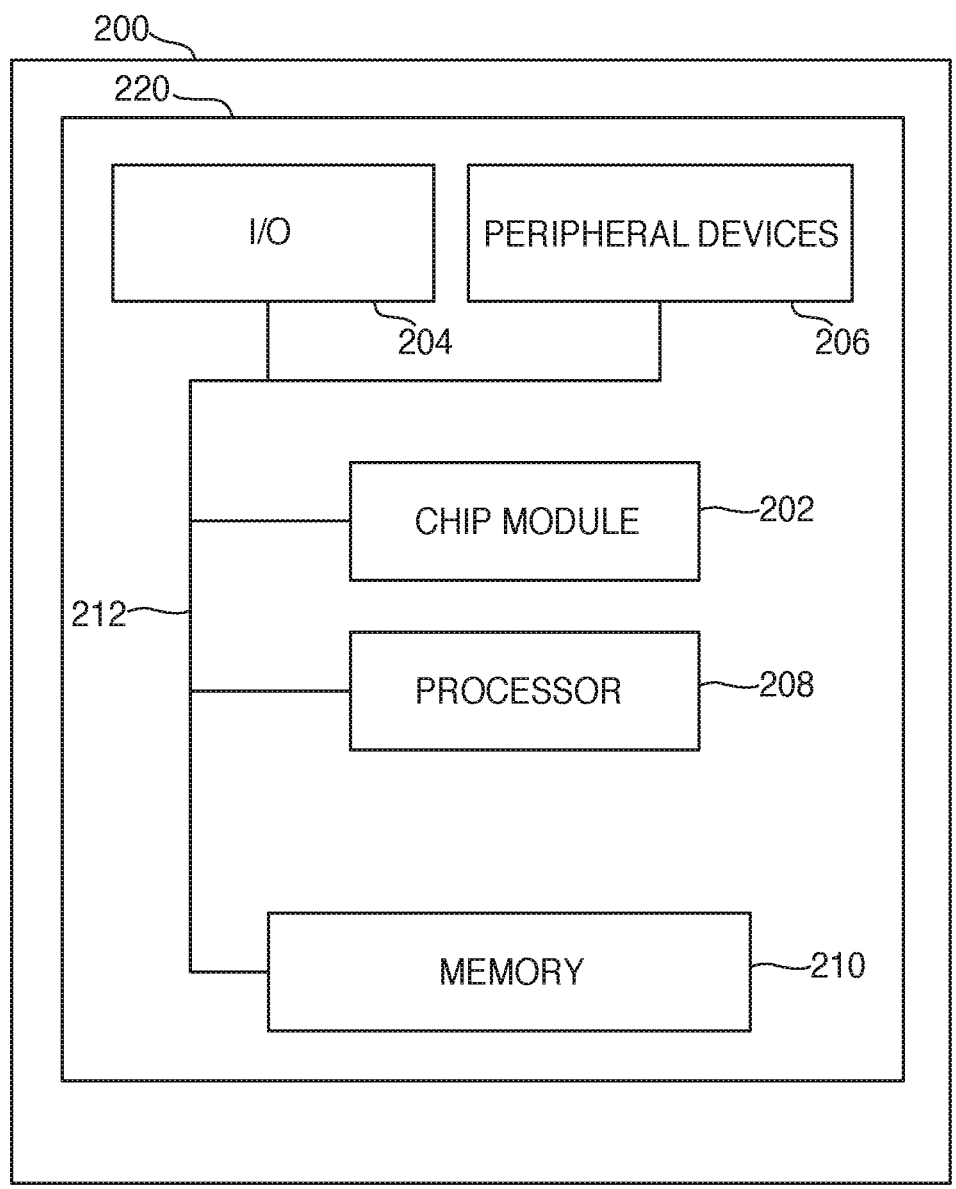
FIG. 2 shows an illustrative apparatus in accordance with principles of the disclosure.

FIG. 2 shows illustrative apparatus 200 that may be configured in accordance with the principles of the disclosure. Apparatus 200 may be a computing machine. Apparatus 200 may include one or more features of the apparatus shown in FIG. 1. Apparatus 200 may include chip module 202, which may include one or more integrated circuits, and which may include logic configured to perform any other suitable logical operations.

Apparatus 200 may include one or more of the following components: I/O circuitry 204, which may include a transmitter device and a receiver device and may interface with fiber optic cable, coaxial cable, telephone lines, wireless devices, PHY layer hardware, a keypad/display control device or any other suitable media or devices; peripheral devices 206, which may include counter timers, real-time timers, power-on reset generators or any other suitable peripheral devices; logical processing device 208, which may compute data structural information and structural parameters of the data; and machine-readable memory 210.

Machine-readable memory 210 may be configured to store in machine-readable data structures: machine executable instructions (which may be alternatively referred to herein as "computer instructions" or "computer code"), applications, signals, and/or any other suitable information or data structures.

Components 202, 204, 206, 208 and 210 may be coupled together by a system bus or other interconnections 212 and may be present on one or more circuit boards such as 220. In some embodiments, the components may be integrated into a single chip. The chip may be silicon-based.

Figure 3:
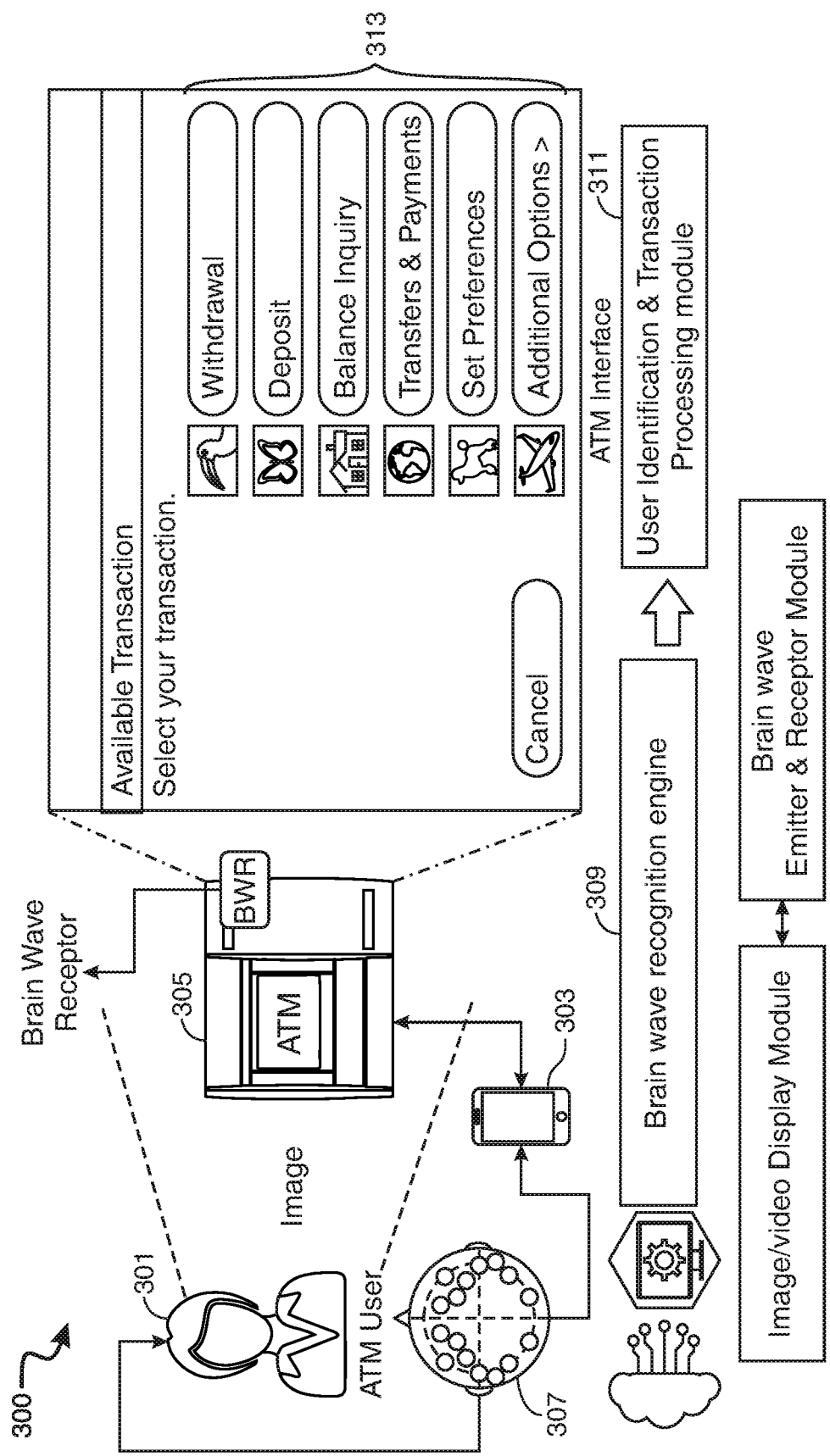
FIG. 3 shows an illustrative system diagram in accordance with principles of the disclosure.

FIG. 3 shows illustrative system diagram 300 in accordance with principles of the disclosure. System diagram 300 shows user 301 interacting with mobile device 303 and ATM 305. EEG device 307 may capture brain wave patterns of user 301 while he or she is presented with a sensory prompt (e.g., an image) via mobile device 303. In certain embodiments, the EEG device may transmit the detected brain waves to the mobile device, which may hash the response to the sensory prompt and transmit the hashed signal to the ATM and/or a central system. The system may process the brain wave pattern (e.g., with engine 309) and compare with signature patterns stored in a user profile in a database (e.g., with module 311). The system may authenticate the user based on the comparison.

The system may also use detected brain wave pattern to process a request of the user. Processing the request may include routing the request. Routing the request may include selecting a transaction option from a list of transaction options 313. Each option from list 313 may be presented next to a different sensory prompt. When the user focuses on the sensory prompt that is next to the desired option, the system may detect a pattern that, by comparison with the signature responses, the system may recognize to be the prompt that is next to the desired option.

Figure 4:
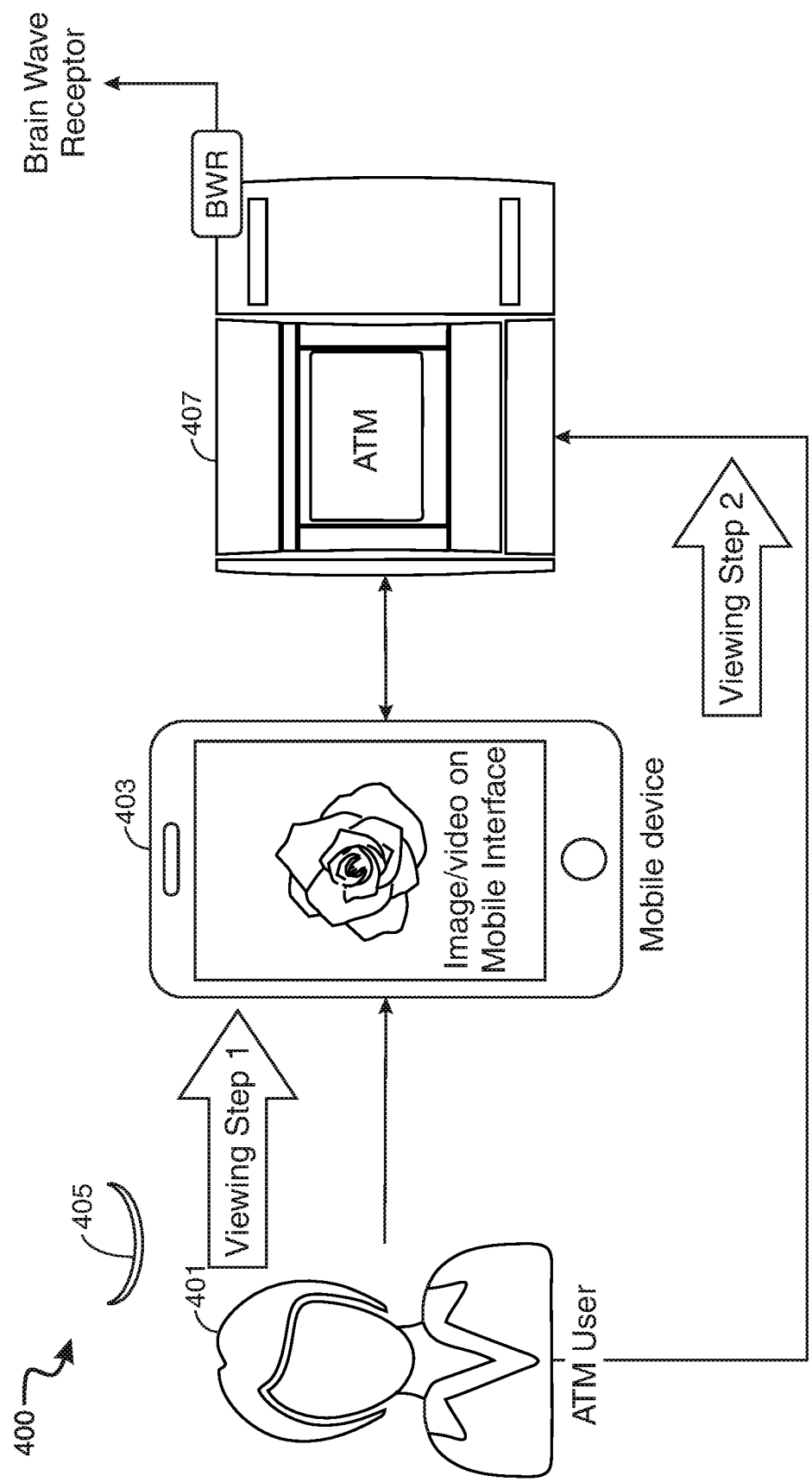
FIG. 4 shows another illustrative system diagram in accordance with principles of the disclosure.

FIG. 4 shows illustrative system diagram 400 in accordance with principles of the disclosure. Diagram 400 shows user 401 viewing an exemplary sensory prompt, shown here as an image of a flower, on mobile device 403. User 401 may be wearing, or otherwise within range of, EEG device 405. EEG device 405 may capture a brain wave response of user

401. EEG device 405 may process the response internally. In some embodiments, the response may be transmitted to mobile device 403. Mobile device 403 may process, hash, and/or transmit the response to ATM 407 and/or a central server.

Figure 5:
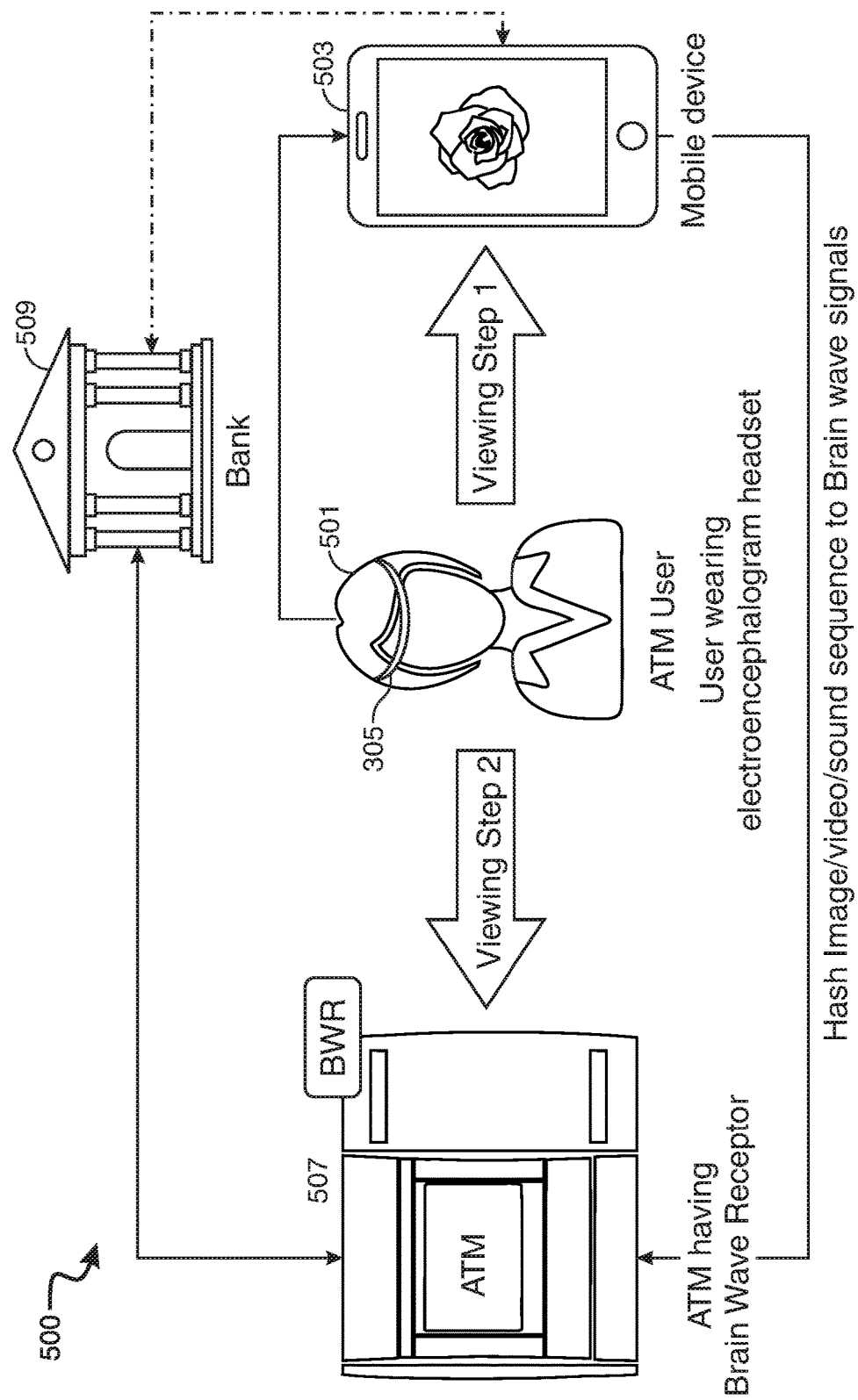
FIG. 5 shows yet another illustrative system diagram in accordance with principles of the disclosure.

FIG. 5 shows illustrative system diagram 500 in accordance with principles of the disclosure. Diagram 500 shows user 501, sensory device 503, EEG device 505, transaction device 507, and central server 509. Central server 509 may be associated with a financial institution.

Figure 6:
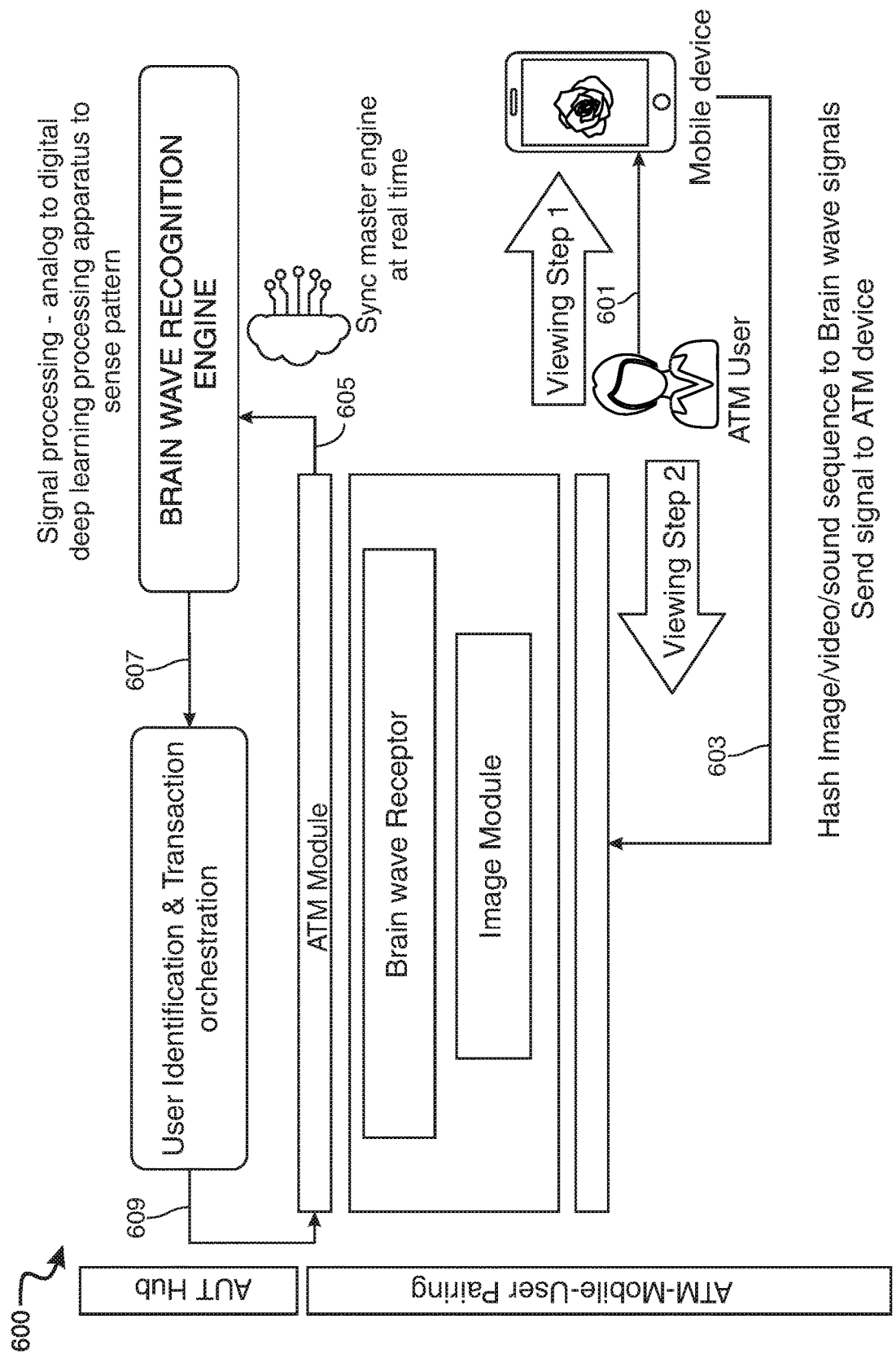
FIG. 6 shows an illustrative flowchart in accordance with principles of the disclosure.

FIG. 6 shows illustrative flowchart 600 in accordance with principles of the disclosure. Flowchart 600 begins at step 601 with a user viewing an image. At step 603, the brain wave pattern may be detected by an EEG device, hashed with the image, and transmitted to an ATM or central server. At step 605, the pattern is processed. Processing may include utilizing analog to digital deep learning apparatus to recognize and/or extract the pattern. Step 607 may include transmitting a digital transaction request along with the pattern and/or the image to a central server, e.g., a financial institution. Step 609 may include authenticating and/or routing the request based, at least in part, on the pattern.

Figure 7:
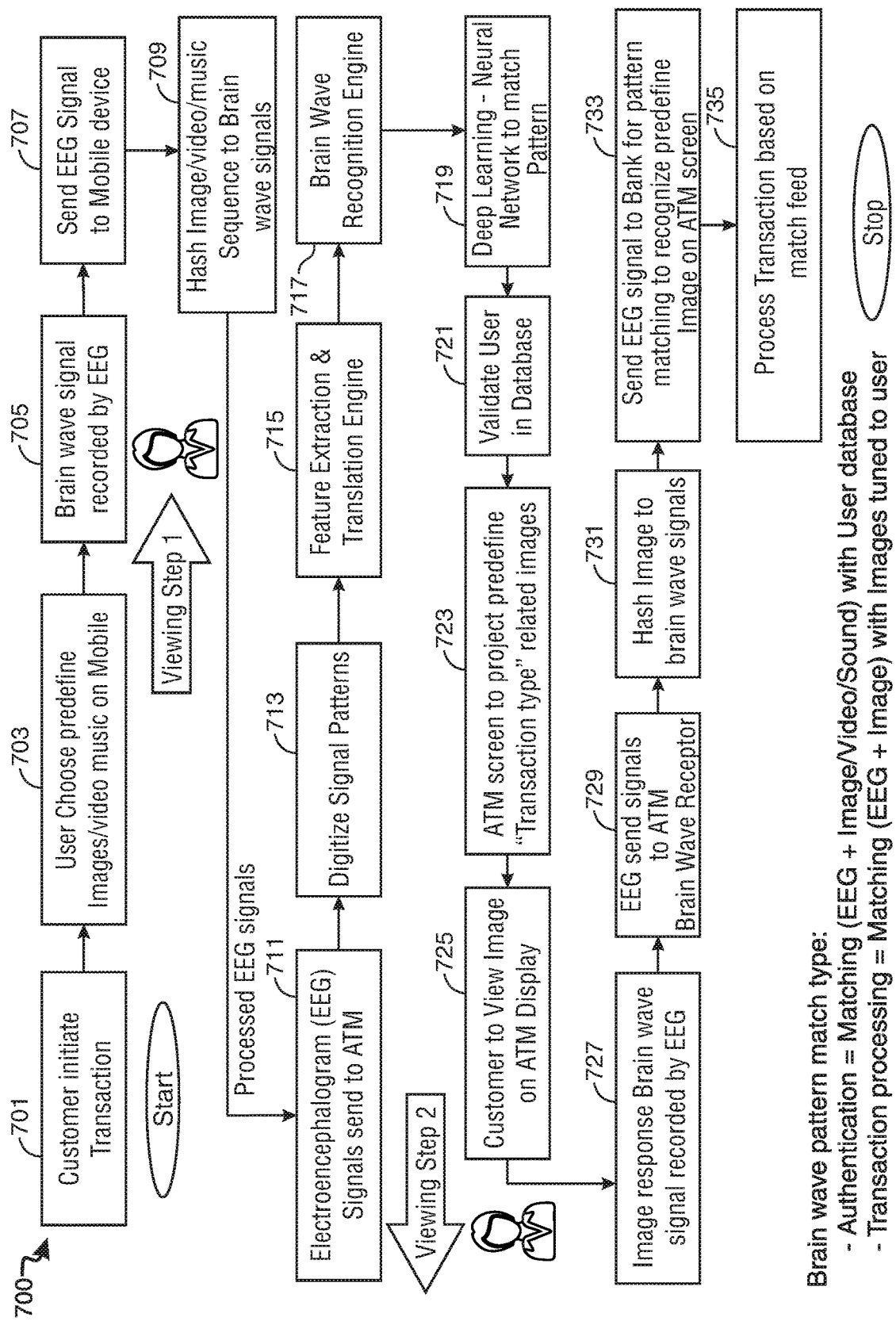
FIG. 7 shows another illustrative flowchart in accordance with principles of the disclosure.

FIG. 7 shows illustrative flowchart 700 in accordance with principles of the disclosure. Step 701 may include a user initiating a transaction. Step 703 may include the user selecting predefined sensory prompts. Step 705 may include recording brain signals of the user via an EEG device. Step 707 may include transmitting the detected signals to a mobile device. Step 709 may include hashing the detected signals with the sensory prompt. Step 711 may include transmitting the hashed signals to an ATM. Step 713 may include digitizing the detected signals. Step 715 may include extracting features via a feature extracting engine. Step 717 may include recognizing brain wave patterns via a brain wave recognition engine. Step 719 may include analyzing the patterns via deep leaning engine and comparing with patterns in a database. Step 721 may include validating and/or authenticating the user based on the comparison.

The disclosed system may also be used to route signals. In some embodiments, the system may perform both authentication and routing. The routing may, in certain embodiments, be performed only after successful authentication. In some embodiments, the system may perform either authentication or routing. In some embodiments, the system may be selectable to perform both authentication and routing, or just one without the other.

Step 723 may include displaying on a transaction device (e.g., an ATM), multiple transaction options in conjunction with multiple sensory prompts. The user may direct the transaction by selecting a transaction option as follows: At step 725 the user may direct his or her attention to the sensory prompt displayed in conjunction with the desired transaction option. At step 727 the EEG device may record the brain signals of the user. At step 729 the brain signals may be transmitted to the ATM and/or a central server. At step 731 the brain signals may be hashed with the sensory prompts and/or the transaction options. At step 733 the hashed signal may be transmitted to a central server. At step 735, the brain waves may be processed. The system may determine, based on the brain wave patterns, which sensory prompt the user was focused on, and thereby may determine the desired transaction option. The transaction may be executed accordingly.

The steps of methods may be performed in an order other than the order shown and/or described herein. Embodiments may omit steps shown and/or described in connection with illustrative methods. Embodiments may include steps that are neither shown nor described in connection with illustrative methods.

Illustrative method steps may be combined. For example, an illustrative method may include steps shown in connection with another illustrative method.

Apparatus may omit features shown and/or described in connection with illustrative apparatus. Embodiments may include features that are neither shown nor described in connection with the illustrative apparatus. Features of illustrative apparatus may be combined. For example, an illustrative embodiment may include features shown in connection with another illustrative embodiment.

The drawings show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

One of ordinary skill in the art will appreciate that the steps shown and described herein may be performed in other than the recited order and that one or more steps illustrated may be optional. The methods of the above-referenced embodiments may involve the use of any suitable elements, steps, computer-executable instructions, or computer-readable data structures. In this regard, other embodiments are disclosed herein as well that can be partially or wholly implemented on a computer-readable medium, for example, by storing computer-executable instructions or modules or by utilizing computer-readable data structures.

Thus, methods and systems for an electroencephalogram hashing device for authentication and routing are provided. Persons skilled in the art will appreciate that the present invention can be practiced by other than the described embodiments, which are presented for purposes of illustration rather than of limitation, and that the present invention is limited only by the claims that follow.

What is claimed is:

1. A secure method for authenticating and routing a digital signal, the method comprising:
   recording a set of signature responses of a user, wherein each signature response from the set of signature responses comprises a pattern of brain activity detected by an electroencephalogram (EEG) when the user is presented with a sensory prompt from a set of sensory prompts, wherein each sensory prompt from the set of sensory prompts corresponds to only one sense selected from a group of sight, hearing, feeling, tasting, or smelling;
   storing a mapping of each signature response of the set of signature responses mapped uniquely to one of the sensory prompts of the set of sensory prompts in a central database as part of a profile of the user;
   receiving a first request from the user to log in to a digital transactional system;
   presenting to the user a first sensory prompt from the set of sensory prompts corresponding to a first sense from the group;
   detecting, via an EEG, a first response of the user to the first sensory prompt, said first response comprising a pattern of brain activity;
   identifying a matching signature response by comparing the first response to one or more of the recorded signature responses stored in the mapping of the profile of the user with the first sensory prompt;

when the first response matches the identified matching signature response within a predetermined delta, authenticating the user to log in to the digital transactional system;
receiving a second request from the user to initiate a transaction;
presenting a plurality of sensory prompts to the user, wherein each of the plurality of sensory prompts is from the set of sensory prompts and corresponds to only a second sense from the group and each of the plurality of sensory prompts is presented in conjunction with a different transaction option from a plurality of transaction options;
detecting, via the EEG, a second response of the user to the plurality of sensory prompts, said second response comprising a pattern of brain activity;
determining which other signature response of the one or more of the recorded signature responses stored in the mapping of the profile of the user is a closest match to the second response;
querying the mapping with the other signature response to determine which sensory prompt is mapped to the other signature response;
determining which transaction option was presented in conjunction with said determined sensory prompt; and
routing the second request to a central server to execute said determined transaction option
wherein one of the first sense and the second sense is the tasting.

2. The method of claim 1, wherein the authenticating comprises matching the first response to the signature response to confirm that the request was transmitted by the user.

3. The method of claim 1, wherein the predetermined delta is a first predetermined delta when authenticating the transaction, and a second predetermined delta when routing the transaction, and the first predetermined delta is smaller than the second predetermined delta.

4. The method of claim 1, wherein the requests are transmitted by the user via an automated teller machine (ATM).

5. The method of claim 1, wherein the sensory prompts are presented to the user via a mobile device.

6. The method of claim 1, further comprising hashing the responses with the sensory prompts to create a hashed signal, and transmitting the hashed signal to the central server for processing.

7. The method of claim 6, wherein the EEG transmits the responses to a mobile device, said mobile device which presented the sensory prompts to the user, and the mobile device performs the hashing and transmits the hashed signal to an automated teller machine (ATM) and/or to the central server.

8. A secure platform for authenticating and routing a digital signal, the platform comprising:
a central database, said central database configured to:
record a set of signature responses of a user, wherein each signature response from the set of signature responses comprises a pattern of brain activity detected by an electroencephalogram (EEG) when the user is presented with a sensory prompt from a set of sensory prompts, wherein each sensory prompt from the set of sensory prompts corresponds to only one sense selected from a group of sight, hearing, feeling, tasting, or smelling;
a transaction device configured to receive a transaction request;
a sensory device configured to present to the user a sensory prompt; and
an EEG device configured to detect brain activity of the user;
wherein, when a request to log in to a digital transactional system is received from the user via the transaction device, the platform is configured to:
present the user, via the sensory device, with a first sensory prompt from the set of sensory prompts corresponding to a first sense from the group;
detect, via the EEG, a first response of the user to the first sensory prompt, said first response comprising a pattern of brain activity;
identify a matching signature response by comparing the first response to one or more of the recorded signature responses stored in the mapping of the profile of the user with the first sensory prompt;
when the first response matches the identified matching signature response within a predetermined delta, authenticating the user to log in to the digital transactional system;
receive a second request from the user to initiate a transaction;
present a plurality of sensory prompts to the user, wherein each of the plurality of sensory prompts is from the set of sensory prompts and corresponds to only a second sense from the group, and each of the plurality of sensory prompts is presented in conjunction with a different transaction option from a plurality of transaction options;
detect, via the EEG, a second response of the user to the plurality of sensory prompts, said second response comprising a pattern of brain activity;
determine which other signature response of the one or more of the recorded signature responses stored in the mapping of the profile of the user is a closest match to the second response;
query the mapping with the other signature response to determine which sensory prompt is mapped to the other signature response;
determine which transaction option was presented in conjunction with said determined sensory prompt; and
route the second request to a central server to execute said determined transaction option
wherein one of the first sense and the second sense is the tasting.

9. The platform of claim 8, wherein authenticating the transaction request comprises matching the first response to the signature response to confirm that the transaction request was transmitted by the user.

10. The platform of claim 8, wherein the predetermined delta is a first predetermined delta when authenticating the transaction, and a second predetermined delta when routing the transaction, and the first predetermined delta is smaller than the second predetermined delta.

11. The platform of claim 8, wherein the transaction device is an automated teller machine (ATM), and the sensory device is a part of the ATM or is a mobile phone running an application.

12. The platform of claim 8, further configured to hash the responses with the sensory prompts to create a hashed signal, and transmit the hashed signal to the central server for processing.

13. The platform of claim 12, wherein the EEG is configured to transmit the responses to the sensory device, and the sensory device is configured to perform the hashing and to transmit the hashed signal to the transaction device and/or to the central server.

\* \* \* \* \*